(12) United States Patent
Sueda et al.

(10) Patent No.: US 9,199,857 B2
(45) Date of Patent: Dec. 1, 2015

(54) ZINC OXIDE PARTICLES, METHOD FOR PRODUCTION OF THE SAME, AND COSMETIC, HEAT RELEASING FILLER, HEAT RELEASING RESIN COMPOSITION, HEAT RELEASING GREASE, AND HEAT RELEASING COATING COMPOSITION COMPRISING THE SAME

(75) Inventors: Satoru Sueda, Fukushima (JP); Mitsuo Hashimoto, Fukushima (JP); Atsuki Terabe, Fukushima (JP); Nobuo Watanabe, Fukushima (JP); Koichiro Magara, Fukushima (JP)

(73) Assignee: Sakai Chemical Industry Co., Ltd., Osaka (JP)

(*) Notice: Subject to any disclaimer, the term of this patent is extended or adjusted under 35 U.S.C. 154(b) by 0 days.

(21) Appl. No.: 14/113,098

(22) PCT Filed: Apr. 26, 2012

(86) PCT No.: PCT/JP2012/061282
§ 371 (c)(1),
(2), (4) Date: Nov. 4, 2013

(87) PCT Pub. No.: WO2012/147888
PCT Pub. Date: Nov. 1, 2012

(65) Prior Publication Data
US 2014/0044971 A1     Feb. 13, 2014

(30) Foreign Application Priority Data
Apr. 28, 2011   (JP) ................ 2011-101023

(51) Int. Cl.
*C01G 9/02*     (2006.01)
*B32B 5/16*     (2006.01)
(Continued)

(52) U.S. Cl.
CPC ............... *C01G 9/02* (2013.01); *A61K 8/0241* (2013.01); *A61K 8/27* (2013.01); *A61Q 1/02* (2013.01);
(Continued)

(58) Field of Classification Search
CPC ....... C01G 9/02; A61K 8/0241; A61K 8/025; A61K 8/04; A61K 8/27
USPC .......................................... 423/622; 428/402
See application file for complete search history.

(56) References Cited

U.S. PATENT DOCUMENTS 5,527,519 A  *  6/1996  Miksits et al. ................ 423/622
7,935,358 B2     5/2011  Sasaki et al.
(Continued)

FOREIGN PATENT DOCUMENTS

JP     H03-183620 A     8/1991
JP     H11-302015 A    11/1999
(Continued)

OTHER PUBLICATIONS

Brochure: ZnO: Ultrafine powder—(downloaded 2014).*
(Continued)

*Primary Examiner* — Holly Le
(74) *Attorney, Agent, or Firm* — Novak Druce Connolly Bove + Quigg LLP (57) ABSTRACT

It is an object of the present invention to provide zinc oxide particles which have excellent ultraviolet blocking performance and also excellent dispersibility, and therefore can be suitably used as an ultraviolet blocking agent for cosmetics. Provided are zinc oxide particles having a primary particle diameter of less than 0.1 μm, an aspect ratio of less than 2.5 and an oil absorption/BET specific surface area of 1.5 ml/100 m² or less.

19 Claims, 6 Drawing Sheets

(51) Int. Cl.

| | |
|---|---|
| *C09C 1/04* | (2006.01) |
| *C08K 3/22* | (2006.01) |
| *C09D 5/18* | (2006.01) |
| *C09D 7/12* | (2006.01) |
| *A61K 8/27* | (2006.01) |
| *A61Q 1/02* | (2006.01) |
| *A61Q 17/04* | (2006.01) |
| *A61K 8/02* | (2006.01) |
| *B82Y 30/00* | (2011.01) |

(52) U.S. Cl.
CPC ............... *A61Q 17/04* (2013.01); *B82Y 30/00* (2013.01); *C08K 3/22* (2013.01); *C09C 1/043* (2013.01); *C09D 5/18* (2013.01); *C09D 7/1266* (2013.01); *C01P 2002/72* (2013.01); *C01P 2004/03* (2013.01); *C01P 2004/04* (2013.01); *C01P 2004/54* (2013.01); *C01P 2004/64* (2013.01); *C01P 2006/12* (2013.01); *C01P 2006/16* (2013.01); *C01P 2006/19* (2013.01); *Y10T 428/2982* (2015.01)

(56) References Cited

U.S. PATENT DOCUMENTS

| | | | |
|---|---|---|---|
| 8,642,018 | B2 | 2/2014 | Kurosawa et al. |
| 9,120,681 | B2 * | 9/2015 | Sueda et al. ............... 1/1 |
| 2006/0127500 | A1 * | 6/2006 | Guidi et al. ............... 424/641 |
| 2009/0017303 | A1 | 1/2009 | Choy et al. |
| 2010/0074837 | A1 * | 3/2010 | Shio et al. ............... 423/622 |
| 2010/0278720 | A1 * | 11/2010 | Wong et al. ............... 423/604 |
| 2011/0081548 | A1 | 4/2011 | Sueda et al. |
| 2011/0081550 | A1 * | 4/2011 | Sueda et al. ............... 428/402 |
| 2014/0058029 | A1 | 2/2014 | Sueda et al. |
| 2014/0112862 | A1 * | 4/2014 | Sueda et al. ............... 423/622 |
| 2014/0214669 | A1 * | 7/2014 | Holenstein et al. ............... 705/44 |

FOREIGN PATENT DOCUMENTS

| | | |
|---|---|---|
| JP | 2008-266445 A | 11/2008 |
| JP | 2009-029698 A | 2/2009 |

OTHER PUBLICATIONS

Paper of Meeting of Taiwanese Ceramic Society (Synthesis Technique of Advanced BaTiO3 Powders for High Capacity MLCC Products) in 2007, with partial English translation.

Garcia, S.P., et al., "Controlling the Morphology of Zinc Oxide Nanorods Crystallized from Aqueous Solutions: The Effect of Crystal Growth Modifiers on Aspect Ratio", *Chemistry of Materials*, 2007, 19, pp. 4016-4022.

Guodong et al., "Study on Preparation and Method of Non-Aggregation Nanometer ZnO", China Ceramics, Term 4, vol. 39, Aug. 2003.

* cited by examiner

Method for measurement of aspect ratio of zinc oxide particles having an indefinite shape: a major axis and a minor axis passing through the center of the major axis are measured for an indefinite shaped zinc oxide particle in the TEM photograph, and an aspect ratio is determined according to the formula:
aspect ratio = average value of major axis/minor axis for 250 particles.

FIG. 10

Aspect ratio of hexagonal plate-shaped zinc oxide particles = (average value of unidirectional diameters of hexagonal-shaped surfaces of 250 particles: L)/(average value of thicknesses of 250 particles: T)

ZINC OXIDE PARTICLES, METHOD FOR PRODUCTION OF THE SAME, AND COSMETIC, HEAT RELEASING FILLER, HEAT RELEASING RESIN COMPOSITION, HEAT RELEASING GREASE, AND HEAT RELEASING COATING COMPOSITION COMPRISING THE SAME

CROSS REFERENCE TO RELATED APPLICATIONS

This application is a National Phase filing under 35 U.S.C. §371 of PCT/JP2012/061282 filed on Apr. 26, 2012; and this application claims priority to Application No. 2011-101023 filed in Japan on Apr. 28, 2011, under 35 U.S.C. §119; the entire contents of all are hereby incorporated by reference.

TECHNICAL FIELD

The present invention relates to zinc oxide particles, method for production of the same, and cosmetic, heat releasing filler, heat releasing resin composition, heat releasing grease, and heat releasing coating composition comprising the same.

BACKGROUND OF THE DISCLOSURE

Zinc oxide particles, which have been used as a sunscreen ultraviolet blocking agent in cosmetic product applications, are ultrafine particles having an average particle diameter of 0.1 µm or less. For example, Patent Documents 1 and 2 disclose zinc oxide fine particles which can be used for ultraviolet blocking agents. These zinc oxide particles are also expected to be modified to have further excellent physical properties.

For example, the zinc oxide fine particles described in Patent Documents 1 and 2 have the problem that particles tend to be aggregated because they are fine particles, so that independency of particles are reduced, leading to an increase in oil absorption. An increase in oil absorption causes the disadvantage that when the particles are compounded in a cosmetic, oil components contained in the cosmetic are absorbed in a large amount, so that the viscosity of the cosmetic is increased. Further, there is also the disadvantage that particles are aggregated, so that dispersibility is deteriorated to reduce transparency, and therefore when a cosmetic containing these particles is used (applied to the skin), it appears unnaturally white. Further, it is also desired to enhance ultraviolet blocking performance and reduce the oil absorption and the volume of a powder.

Patent Document 3 discloses a production method in which a mixed liquid of a zinc compound, acetic acid and glycol is held at a temperature of 50 to 200° C. for 0.5 to 5 hours to generate zinc oxide fine particles having an average particle diameter of 200 nm or less. However, this production method is a method of obtaining a precipitate by heating a solution in which zinc oxide is fully dissolved, and zinc oxide particles obtained by this method are not preferable because particles having an aspect ratio of less than 2.5 cannot be obtained. Further, the production method is not suitable from an industrial point of view because expensive glycol is used.

PRIOR TECHNICAL DOCUMENTS

Patent Documents

[Patent Document 1] Japanese Kokai Publication Hei11-302015

[Patent Document 2] Japanese Kokai Publication Hei3-183620

[Patent Document 3] Japanese Kokai Publication 2009-29698

SUMMARY OF INVENTION

Problems to be Solved by the Invention

It is an object of the present invention to provide zinc oxide particles which have excellent ultraviolet blocking performance and visible light transparency, and also excellent dispersibility, and therefore can be suitably used as an ultraviolet blocking agent for cosmetics.

Means for Solving Object

The present invention relates to zinc oxide particles having a primary particle diameter of less than 0.1 µm, an aspect ratio of less than 2.5 and an oil absorption/BET specific surface area of 1.5 ml/100 m$^2$ or less.

The zinc oxide particles are preferably those obtained by a production method including a step of aging zinc oxide fine particles in water in which a zinc salt is dissolved.

Preferably, the zinc oxide particles have a total light transmittance of 20% or less at a wavelength of 310 nm, a total light transmittance of 20% or less at a wavelength of 350 nm, a parallel light transmittance of 70% or more at a wavelength of 500 nm and a parallel light transmittance of 70% or more at a wavelength of 700 nm when a coating film prepared using the zinc oxide particles described above is measured by a spectrophotometer V-570 (manufactured by JASCO Corporation).

Preferably, the zinc oxide particles have an apparent density of 0.26 g/ml or more.

Preferably, the zinc oxide particles have a sharpened gloss (20° gloss) of 110 or more as a coating film.

The present invention also provides a method for production of the zinc oxide particles described above, the method including a step of aging zinc oxide fine particles in water in which a zinc salt is dissolved.

The present invention also provides a cosmetic containing the zinc oxide particles described above.

The present invention also provides a heat releasing filler made of the zinc oxide particles described above.

The present invention also provides a heat releasing resin composition containing the zinc oxide particles described above.

The present invention also provides a heat releasing grease containing the zinc oxide particles described above.

The present invention also provides a heat releasing coating composition containing the zinc oxide particles described above.

Effects of the Invention

The zinc oxide particles of the present invention have high dispersibility, a low oil absorption and a high apparent density while exhibiting excellent ultraviolet blocking performance and visible light transparency when compounded in a cosmetic. The zinc oxide particles exhibit excellent heat releasing performance when used as a heat releasing filler.

DETAILED DESCRIPTION OF PREFERRED EMBODIMENTS

The present invention will be described in detail hereinafter.

The zinc oxide particles of the present invention are zinc oxide particles having a primary particle diameter of less than 0.1 μm, an aspect ratio of less than 2.5 and an oil absorption/BET specific surface area of 1.5 ml/100 m² or less. Conventional zinc oxide fine particles tend to be aggregated, so that the oil absorption is increased, and dispersibility is insufficient, and therefore it is difficult to maintain stability of a system. The present invention makes it possible to achieve both excellent ultraviolet blocking performance as zinc oxide particles and excellent visible light transparency achieved due to high independency and dispersibility of particles by ensuring that the aspect ratio and the oil absorption/BET specific surface area fall within the ranges described above.

The zinc oxide particles of the present invention have a primary particle diameter of less than 0.1 μm. That is, the zinc oxide particles have a particle diameter comparable to that of zinc oxide fine particles which have been commonly used as an ultraviolet blocking agent for cosmetics. The primary particle diameter in the present invention corresponds to a diameter of a sphere having the same surface area as a specific surface area determined by a BET method. That is, the primary particle diameter is a value determined according to the relational expression:

primary particle diameter (μm)=[6/($Sg \times \rho$)]

($Sg$ (m²/g): specific surface area, $\rho$ (g/cm³): true specific gravity of particle.

The specific surface area: $Sg$ by the BET method was measured using a fully automatic BET specific surface area measuring device Macsorb (manufactured by Mountech Co., Ltd.), and the measurement value was used for the calculation described above. As the true specific gravity of particle: $\rho$, a value of the true specific gravity of zinc oxide, i.e. 5.6, was used for the above calculation.

The primary particle diameter is more preferably 0.005 μm or more and less than 0.1 μm.

A value shown as crystallite diameter/primary particle diameter herein is a value as an indicator of a level of independency of primary particles that form a powder. The primary particle diameter is a geometric particle diameter corresponding to a diameter of a sphere having the same surface area as a specific surface area determined by a BET method as described previously. On the other hand, the crystallite diameter is a value determined from a half width of a diffraction peak of the (101) plane of zinc oxide in the X-ray diffraction pattern as described below. Therefore, as the value of crystallite diameter/primary particle diameter becomes closer to 1, a difference between the geometric particle diameter and the single crystal size decreases, which means that primary particles are not aggregated particles, but exist independently as single crystal particles.

For the crystallite diameter (μm) herein, results of performing analysis using an X-ray diffractometer UltimaIII (manufactured by Rigaku Corporation) having an X-ray tube with copper are shown. The crystallite usually means a small single crystal in a microscopic level, which forms a crystalline substance. Herein, the crystallite diameter (μm) is a value determined from a half width of a diffraction peak of the (101) plane of zinc oxide in the X-ray diffraction pattern of a hexagonal wurtzite-type zinc oxide particle.

Figure 9:
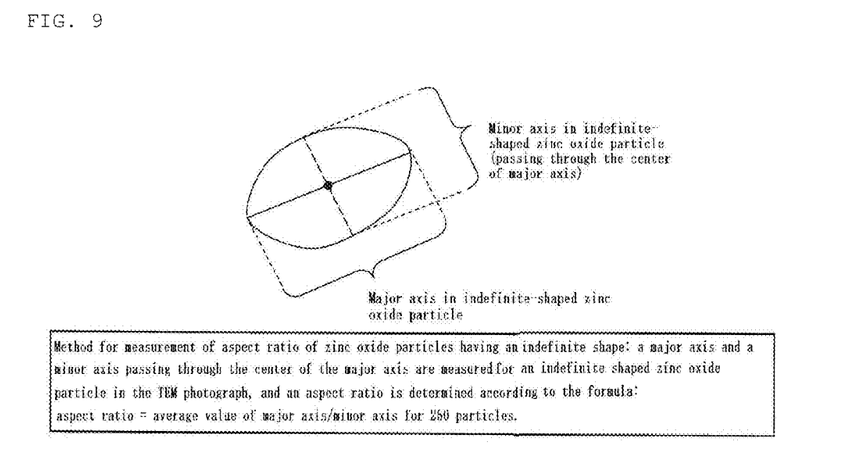
FIG. 9 is an explanatory view for a method for measurement of an aspect ratio of zinc oxide particles of the present invention.
Figure 10:
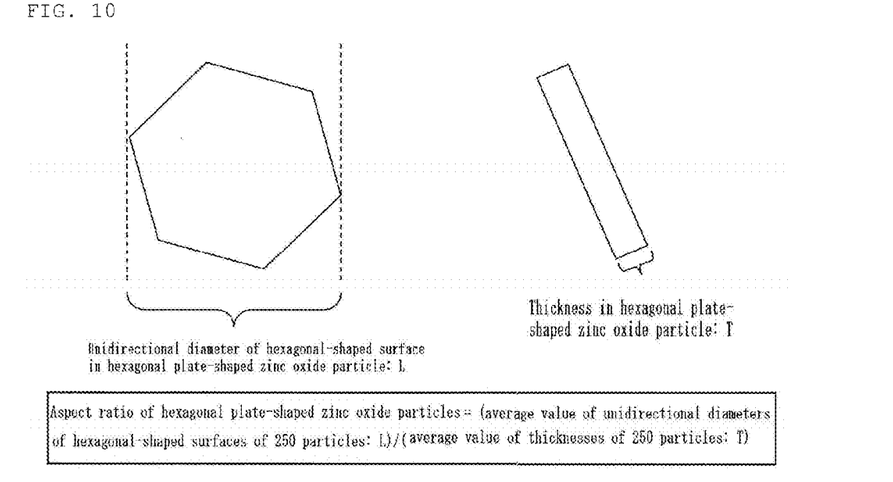
FIG. 10 is an explanatory view for a method for measurement of an aspect ratio of hexagonal plate-shaped zinc oxide particles of comparative examples.
Figure 11:
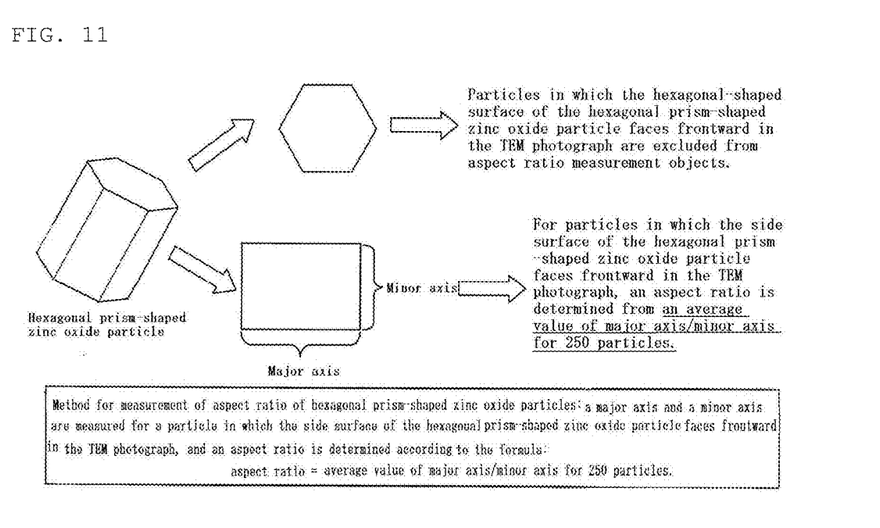
FIG. 11 is an explanatory view for a method for measurement of an aspect ratio of hexagonal prism-shaped zinc oxide particles of comparative examples.

Further, the zinc oxide particles of the present invention have an aspect ratio of less than 2.5 and an oil absorption/BET specific surface area of 1.5 ml/100 m² or less. The zinc oxide particles described above can exhibit high independency and dispersibility. In the present invention, a ratio between the lengths of a major axis and a minor axis passing through the major axis: major axis/minor axis was measured for 250 primary particles of zinc oxide particles in a visual field of 20000 to 50000 magnification in a transmission electron microscope (TEM, JEM-1200EX II, manufactured by JEOL Ltd.) photograph, and an average value of a cumulative distribution thereof was defined as an aspect ratio. The aspect ratio is more preferably 2.0 or less. The method for measurement of an aspect ratio of the zinc oxide particles of the present invention is shown in FIG. 9.

The zinc oxide particles of the present invention have an oil absorption/BET specific surface area of 1.5 ml/100 m² or less. It is preferable that the oil absorption/BET specific surface area is 1.5 ml/100 m² or less because when the particles are mixed with, for example, a resin, oil or the like and made to blend therewith, they can be made to blend with a smaller amount of the resin or oil, and the viscosity of a cosmetic obtained in this way can be decreased. Further, when the value of the oil absorption/BET specific surface area is decreased, the concentration of zinc oxide in the cosmetic can be increased. The oil absorption/BET specific surface area is more preferably 1.3 ml/100 m² or less. The oil absorption (ml/100 g) in the oil absorption/BET specific surface area is a value measured by the method described in Pigment Test Method-Oil Absorption in JIS K 5101-13-2. As an oil, isopropyl myristate (EXCEPARL IPM manufactured by Kao Corporation) was used in place of boiled linseed oil. The BET specific surface area (m²/g) in the oil absorption/BET specific surface area is a value measured using a fully automatic BET specific surface area measuring device Macsorb (manufactured by Mountech Co., Ltd.). The oil absorption/BET specific surface area (ml/100 m²) is a value obtained by dividing the value of the oil absorption (ml/100 g) by the value of the BET specific surface area (m²/g), and as this value becomes smaller, the oil absorption per unit area of the particle surface is low, leading to reduced aggregation of particles, and enhanced independency and dispersibility of particles.

Preferably, the zinc oxide particles of the present invention have a total light transmittance of 20% or less at a wavelength of 310 nm, a total light transmittance of 20% or less at a wavelength of 350 nm, a parallel light transmittance of 70% or more at a wavelength of 500 nm and a parallel light transmittance of 70% or more at a wavelength of 700 nm when a coating film prepared using the zinc oxide particles of the present invention is measured by a spectrophotometer V-570 (manufactured by JASCO Corporation). An ultraviolet blocking effect to ultraviolet rays having a wavelength of UVB is enhanced as the value of total light transmittance at a wavelength of 310 nm becomes smaller, and an ultraviolet blocking effect to ultraviolet rays having a wavelength of UVA is enhanced as the value of total light transmittance at a wavelength of 350 nm becomes smaller. Visible light transparency is enhanced as the values of parallel light transmittances at wavelengths of 500 nm and 700 nm become larger. That is, it is preferable that the particles show a total light transmittance and a parallel light transmittance in the ranges described above because it is indicated that the particles have excellent ultraviolet blocking performance and transparency.

The total light transmittance and parallel light transmittance described above can be measured by the following method. In a mayonnaise bottle having a volume of 75 ml, 2 g of zinc oxide particles, 10 g of varnish (ACRYDIC A-801-P manufactured by DIC Corporation), 5 g of butyl acetate (special grade reagent, manufactured by Wako Pure Chemical Industries, Ltd.), 5 g of xylene (genuine special grade, manufactured by JUNSEI CHEMICAL CO., LTD.) and 38 g of glass beads (1.5 mm, manufactured by Potters-Ballotini Co., Ltd.) are put and sufficiently mixed, then fixed in a paint conditioner Model 5410 (manufactured by RED DEVIL, Inc.), and subjected to a dispersion treatment by giving vibrations for 90 minutes, thereby preparing a coating. Next, a small amount of the prepared coating is added dropwise onto a slide glass (length/width/thickness=76 mm/26 mm/0.8 to 1.0 mm, manufactured by Matsunami Glass Ind., Ltd.), a coating film is prepared using a bar coater (No. 579 ROD No. 6, manufactured by YASUDA SEIKI SEISAKUSHO, LTD.), and the prepared coating film is measured by a spectrophotometer V-570 (manufactured by JASCO Corporation).

Preferably, the zinc oxide particles of the present invention have an apparent density of 0.26 g/ml or more. An apparent density of 0.26 g/ml or more is preferable because the volume of a powder decreases, so that a large amount of the powder can be transported, for example, at the time of transportation. Further, an apparent density of 0.26 g/ml or more is preferable because handling as a powder becomes easy, i.e. mixing can be performed in a container having a smaller volume during mixing with other components. The apparent density is more preferably 0.3 g/ml or more. Herein, the apparent density is a value measured by the method described in Pigment Test Method-Apparent Density or Apparent Specific Volume (Standing Method) in JIS K 5101-12-1. The volume of the powder decreases as the apparent density increases.

Preferably, the zinc oxide particles of the present invention have a sharpened gloss (20° gloss) of 110 or more as a coating film. Here, the sharpened gloss (20° gloss) of the coating film is a value obtained from the coating film used in measurement of the total light transmittance and parallel light transmittance described above using GLOSS METER GM-26D (manufactured by MURAKAMI COLOR RESEARCH LABORATORY CO., Ltd.), and is a value of glossiness at an incidence angle of 20°. A larger value of sharpened gloss (20° gloss) corresponds to reduced aggregation and enhanced dispersibility of zinc oxide particles in the prepared coating film.

It is preferable that the sharpened gloss (20° gloss) is 110 or more because an excellent sense of transparency can be imparted to the finish when the particles are compounded in, for example, a cosmetic. The sharpened gloss (20° gloss) is more preferably 115 or more.

The method for production of the zinc oxide particles described above is not particularly limited, and they can be obtained by, for example, a production method including a step of aging zinc oxide fine particles in water in which a zinc salt is dissolved. Such a method for production of zinc oxide particles is a part of the present invention. By this production method, zinc oxide particles can be obtained directly without passing through a thermal decomposition step such as that of calcinating. However, calcinating may be performed for the purpose of enhancing crystallinity, and so on.

In this production method, unlike a method of performing aging after forming particles by neutralization of a zinc salt compound as described in the cited documents, zinc oxide particles are added as a seed (seed crystal), and therefore particles are grown as the surface layers thereof are repeatedly dissolved and precipitated while zinc oxide fine particles as a seed serve as cores. Thus, the particle diameters of zinc oxide particles obtained after aging using, as a base, zinc oxide fine particles as cores are determined, and particle shapes and particle diameters are established in a uniform state. Therefore, the above-mentioned method is preferable in that the particle shape and the particle diameter are more precisely controlled, and independency and dispersibility of particles are enhanced. Even if zinc oxide fine particles used as a raw material are poor in uniformity in terms of particle diameter distribution and particle shape, the uniformity of the particle diameter distribution and particle shape is enhanced by performing treatments in the production method described above. Further, independency and dispersibility of particles are enhanced, so that zinc oxide particles having excellent physical properties can be obtained.

By adjusting an aging temperature, an aging time, a zinc salt concentration, a zinc oxide fine particle concentration and so on as necessary, the particle diameter and shape, and the like can be adjusted.

In production of zinc oxide particles as described above, zinc oxide fine particles are used. The zinc oxide fine particle is not particularly limited, but its particle diameter is preferably 0.005 μm or more and 0.05 μm or less. The particle diameter of the zinc oxide fine particle corresponds to a diameter of a sphere having the same surface area as a specific surface area determined by a BET method. That is, the particle diameter is a value determined by the following calculation formula from a specific surface area: Sg determined by making a measurement using a fully automatic BET specific area measuring device Macsorb (manufactured by Mountech Co., Ltd.), and a true specific gravity of zinc oxide: ρ.

particle diameter (μm)=$[6/(Sg \times \rho)]$ ($Sg$ (m$^2$/g): specific surface area, $\rho$ (g/cm$^3$): true specific gravity of particle)

It is to be noted that as the true specific gravity of particle: ρ, a value of 5.6, which is a value of the true specific gravity of zinc oxide, was used for the above calculation.

Zinc oxide fine particles that can be used as a raw material are not particularly limited, and zinc oxide produced by a known method can be used. Examples of those that are commercially available may include FINEX-75, FINEX-50 and FINEX-30 manufactured by Sakai Chemical Industry Co., Ltd.

In the method for production of zinc oxide particles according to the present invention, the zinc oxide fine particles are aged in water in which a zinc salt is dissolved.

That is, the zinc oxide fine particles are dispersed in an aqueous zinc salt solution, and heated in this state to be crystal-grown.

The solvent to be used in the present invention is water. Water is inexpensive and safe in terms of handling, and is therefore most preferable from the viewpoint of production control and costs.

The aqueous zinc salt solution to be used is not particularly limited, and examples thereof may include aqueous solutions of zinc acetate, zinc nitrate, zinc sulfate, zinc chloride and zinc formate. Particularly when an aqueous zinc acetate solution, among the aqueous zinc salt solutions, is used, specific zinc oxide particles of the present invention can be suitably obtained.

These aqueous zinc salt solutions may be those prepared by mixing zinc oxide, an acid and water to acid-hydrolyze zinc oxide. The particle shape and particle size of zinc oxide to be used when the aqueous zinc salt solution is prepared with zinc oxide, an acid and water are not particularly limited, but the Zn purity of zinc oxide is preferably 95% or more for reducing impurities as much as possible. Examples of the acid include acetic acid, nitric acid, sulfuric acid, hydrochloric acid, formic acid, citric acid, oxalic acid, propionic acid, malonic acid, lactic acid, tartaric acid, gluconic acid and succinic acid, and particularly when acetic acid is used, specific zinc oxide particles of the present invention can be suitably obtained. Two of these aqueous zinc salt solutions may be used in combination.

The zinc salt concentration in an aqueous zinc salt solution to be used is preferably 0.005 mol/l or more and less than 0.30 mol/l.

When zinc oxide fine particles are added in the aqueous zinc salt solution to form a slurry, the concentration of zinc oxide fine particles is preferably 10 to 500 g/l based on the total amount of the slurry.

The method for preparation of a slurry is not particularly limited, and for example, a homogeneous slurry having a zinc oxide fine particle concentration of 10 to 500 g/l can be formed by adding the above-described components to water, and dispersing the components at 5 to 30° C. for 10 to 30 minutes.

In the aging described above, components other than zinc oxide fine particles, a zinc salt and water may be added in a small amount within the bounds of not impairing the effect of the present invention. For example, a dispersant and the like may be added.

Preferably, aging is performed at 45 to 110° C. Particularly, the aging time may be 0.5 to 24 hours. The particle diameter can be adjusted by conditions such as an aging temperature, an aging time, a zinc oxide fine particle concentration and a zinc salt concentration, and therefore it is preferable to appropriately set these conditions according to intended zinc oxide particles.

Zinc oxide particles thus obtained may be subjected to post-treatments such as filtration, water washing and drying as necessary.

Zinc oxide particles produced by the above-described method may be classified by sieving as necessary. Examples of methods for classification by sieving may include wet classification and dry classification. Further, a treatment such as wet crushing or dry crushing may be performed.

As described above, the method for production of zinc oxide particles according to the present invention is capable of obtaining zinc oxide particles without performing a calcinating treatment, but zinc oxide particles obtained by the above-described method may be subjected to a calcinating treatment. For calcinating, mention may be made of a known method using an arbitrary device, and treatment conditions and the like are not particularly limited.

The zinc oxide particles of the present invention may be further surface-treated as necessary. The surface treatment is not particularly limited, and examples thereof may include known treatment methods such as inorganic surface treatments to form an inorganic oxide layer such as a silica layer, an alumina layer, a zirconia layer or a titania layer, and various kinds of other surface treatments. Two or more kinds of surface treatments may be sequentially performed.

More specific examples of the surface treatment may include surface treatments with a surface treatment agent selected from an organic silicon compound, an organic aluminum compound, an organic titanium compound, a higher fatty acid, a higher fatty acid ester, a metallic soap, a polyhydric alcohol and an alkanolamine. For the surface treatment agent described above, a treatment amount can be appropriately set according to the particle diameter of the zinc oxide particle.

Examples of the organic silicon compound may include organopolysiloxanes such as methyl hydrogen polysiloxane and dimethyl polysiloxane, and silane coupling agents such as triethoxyvinylsilane and diphenyldimethoxysilane.

Examples of the higher fatty acid may include higher fatty acids having 10 to 30 carbon atoms, such as lauric acid, stearic acid and palmitic acid.

Examples of the higher fatty acid ester may include alkyl esters of the above-described higher fatty acids, such as octyl palmitate.

Examples of the metallic soap may include metal salts of the above-described higher fatty acids, such as aluminum stearate and aluminum laurate. The metal species that forms the metallic soap is not particularly limited, and examples thereof may include aluminum, lithium, magnesium, calcium, strontium, barium, zinc and tin.

Examples of the polyhydric alcohol may include trimethylolethane, trimethylolpropane and pentaerythritol.

Examples of the alkanolamine may include diethanolamine, dipropanolamine, triethanolamine and tripropanolamine.

The treatment with the surface treatment agent can be achieved by mixing a predetermined amount of the surface treatment agent with the zinc oxide particles. Further, the treatment can be achieved by adding the zinc oxide particles to an appropriate medium, for example, water, an alcohol, an ether or the like to be suspended, adding a surface treatment agent to the suspension, followed by stirring, separating, drying and crushing the suspension, or solidifying by evaporation and crushing the suspension.

Since zinc oxide particles subjected to the surface treatment described above have various kinds of coating layers such as those of zinc silicate on the surfaces thereof, the physiological activity and chemical activity thereof are suppressed when the zinc oxide particles are compounded in a cosmetic, and therefore a particularly excellent cosmetic product can be provided.

The zinc oxide particles of the present invention are not particularly limited for applications thereof, and can be suitably used in, for example, applications of raw materials of cosmetics and heat releasing fillers. These cosmetics and heat releasing fillers are a part of the present invention.

A cosmetic containing the zinc oxide particles of the present invention has high ultraviolet blocking performance, and is excellent in dispersibility and stability.

Examples of the cosmetic of the present invention may include a foundation, a makeup base, an eye shadow, a rouge, a mascara, a lipstick and a sunscreen agent. The cosmetic of the present invention can be in any form such as that of an oily cosmetic, an aqueous cosmetic, an O/W type cosmetic or a W/O type cosmetic. Above all, the cosmetic of the present invention can be suitably used in sunscreen agents.

For the cosmetic of the present invention, any aqueous component or oily component that can be used in the field of cosmetics can be used in combination in addition to components that form the above-described mixture. The aqueous component and oily component described above are not particularly limited, and examples thereof may include those containing components such as oils, surfactants, moisturizers, higher alcohols, sequestrants, natural and synthetic polymers, water-soluble and oil-soluble polymers, UV blocking agents, various extracts, inorganic and organic pigments, inorganic and organic clay minerals, inorganic and organic pigments treated with metallic soap or silicone, coloring materials such as organic dyes, preservatives, antioxidants, dyes, thickeners, pH adjusters, perfumes, cooling-sensation agents, antiperspirants, disinfectants, and skin activators. Specifically, a desired cosmetic can be produced in the usual manner using any one or more of the components listed below. The amounts of these components incorporated are not particularly limited as long as they do not interfere with the effects of the present invention.

The oil is not particularly limited, and examples thereof may include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, arachis oil, tea seed oil, kaya oil, rice bran oil, Chinese tung oil, Japanese tung oil, jojoba oil, germ oil, triglycerol, glycerol trioctanoate, glycerol triisopalmitate, cacao butter, coconut oil, horse fat, hydrogenated coconut oil, palm oil, beef tallow, mutton tallow, hydrogenated beef tallow, palm kernel oil, lard, beef bone fat, Japan wax kernel oil, hydrogenated oil, neatsfoot oil, Japan wax, hydrogenated castor oil, beeswax, candelilla wax, cotton wax, carnauba wax, bayberry wax, insect wax, spermaceti wax, montan wax, bran wax, lanolin, kapok wax, lanolin acetate, liquid lanolin, sugarcane wax, isopropyl lanolate, hexyllaurate, reduced lanolin, jojoba wax, hard lanolin, shellac wax, POE lanolin alcohol ether, POE lanolin alcohol acetate, POE cholesterol ether, polyethylene glycol lanolate, POE hydrogenated lanolin alcohol ether, liquid paraffin, ozokerite, pristane, paraffin, ceresin, squalene, Vaseline, and microcrystalline wax.

The lipophilic nonionic surfactant is not particularly limited, and examples thereof may include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerin polyglycerin fatty acids such as glycerol mono-cottonseed oil fatty acid, glycerol monoerucate, glycerol sesquioleate, glycerol monostearate, α,α'-glycerol oleate pyroglutamate, and glycerol monostearate malate; propylene glycol fatty acid esters such as propylene glycol monostearate; hydrogenated castor oil derivatives; and glycerol alkyl ethers.

The hydrophilic nonionic surfactant is not particularly limited, and examples thereof may include POE sorbitan fatty acid esters such as POE sorbitan monostearate, POE sorbitan monooleate and POE sorbitan tetraoleate; POE sorbitol fatty acid esters such as POE sorbitol monolaurate, POE sorbitol monooleate, POE sorbitol pentaoleate and POE sorbitol monostearate; POE glycerin fatty acid esters such as POE glycerin monostearate, POE glycerin monoisostearate and POE glycerin triisostearate; POE fatty acid esters such as POE monooleate, POE distearate, POE monodioleate and ethylene glycol distearate; POE alkyl ethers such as POE lauryl ether, POE oleyl ether, POE stearyl ether, POE behenyl ether, POE 2-octyldodecyl ether and POE cholestanol ether; POE alkyl phenyl ethers such as POE octyl phenyl ether, POE nonyl phenyl ether and POE dinonyl phenyl ether; Pluaronic types such as Pluronic; POE/POP alkyl ethers such as POE/POP cetyl ether, POE/POP 2-decyltetradecyl ether, POE/POP monobutyl ether, POE/POP hydrogenated lanolin and POE/POP glycerin ether; tetra-POE/tetra-POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester and POE hydrogenated castor oil maleic acid; POE beeswax/lanolin derivatives such as POE sorbitol beeswax; alkanolamides such as coconut oil fatty acid diethanolamide, lauric acid monoethanolamide and fatty acid isopropanol amide; POE propylene glycol fatty acid esters; POE alkylamines; POE fatty acid amides; sucrose fatty acid esters; POE nonylphenyl formaldehyde condensation products; alkyl ethoxy dimethylamine oxides; and trioleyl phosphoric acid.

Examples of other surfactants include anionic surfactants such as fatty acid soaps, higher-alkyl sulfuric ester salts, POE triethanolamine lauryl sulfate, and alkyl ether sulfuric ester salts; cationic surfactants such as alkyl trimethylammonium salts, alkyl pyridinium salts, alkyl quaternary ammonium salts, alkyl dimethylbenzyl ammonium salts, POE alkylamines, alkylamine salts, and polyamine fatty acid derivatives; and amphoteric surfactants such as imidazoline amphoteric surfactants and betaine surfactants. They may be incorporated within the bounds of not causing any problems with stability and skin irritation.

The moisturizer is not particularly limited, and examples thereof may include xylitol, sorbitol, maltitol, chondroitin sulfate, hyaluronic acid, mucoitinsulfuric acid, caronic acid, atelocollagen, cholesteryl-12-hydroxystearate, sodium lactate, bile salts, dl-pyrrolidone carboxylate, short-chain soluble collagens, diglycerol (EO) PO adducts, Rosa roxburghii extract, yarrow extract, and melilot extract.

The higher alcohol is not particularly limited, and examples thereof may include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerol ether (batyl alcohol), 2-decyltetradecynol, lanolin alcohol, cholesterol, phytosterol, hexyldodecanol, isostearyl alcohol, and octyldodecanol.

The sequestrant is not particularly limited, and examples thereof may include 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

The natural water-soluble polymer is not particularly limited, and examples thereof may include plant-derived polymers such as gum arabic, tragacanth gum, galactan, guar gum, carob gum, karaya gum, carrageenan, pectin, agar, quince seed (quince), algal colloid (algal extract), starch (rice, corn, potato, wheat), and glycyrrhizinic acid; microorganism-derived polymers such as xanthan gum, dextran, succinoglucan, and pullulan; and animal-derived polymers such as collagen, casein, albumin, and gelatin.

The semisynthetic water-soluble polymer is not particularly limited, and examples thereof may include starch polymers such as carboxymethyl starch and methyl hydroxypropyl starch; cellulose polymers such as methyl cellulose, nitro cellulose, ethyl cellulose, methyl hydroxypropyl cellulose, hydroxyethyl cellulose, cellulose sodium sulfate, hydroxypropyl cellulose, sodium carboxymethylcellulose (CMC), crystalline cellulose, and cellulose powder; and alginate polymers such as sodium alginate and propylene glycol alginate.

The synthetic water-soluble polymer is not particularly limited, and examples thereof may include vinyl polymers such as polyvinyl alcohol, polyvinyl methyl ether, and polyvinyl pyrrolidone; polyoxyethylene polymers such as polyethylene glycol 20,000, polyethylene glycol 40,000, and polyethylene glycol 60,000; copolymers such as polyoxyethylene-polyoxypropylene copolymers; acrylic polymers such as sodium polyacrylate, polyethylacrylate, and polyacrylamide; polyethyleneimine; and cationic polymers.

The inorganic water-soluble polymer is not particularly limited, and examples thereof may include bentonite, magnesium aluminum silicate (Veegum), laponite, hectorite, and silicic anhydride.

The ultraviolet blocking agent is not particularly limited, and examples thereof may include benzoic acid-based ultraviolet blocking agents such as paraaminobenzoic acid (hereinafter, abbreviated as PABA), PABA monoglycerin ester, N,N-dipropoxy PABA ethyl ester, N,N-diethoxy PABA ethyl ester, N,N-dimethyl PABA ethyl ester and N,N-dimethyl PABA butyl ester; anthranilic acid-based ultraviolet blocking agents such as homomenthyl-N-acetyl anthranilate; salicylic acid-based ultraviolet blocking agents such as amyl salicylate, menthyl salicylate, homomenthyl salicylate, octyl salicylate, phenyl salicylate, benzyl salicylate and p-isopropanol phenyl salicylate; cinnamic acid-based ultraviolet blocking agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate and glycerylmono-2-ethylhexanoyl-di-paramethoxy cinnamate; benzophenone-based ultraviolet blocking agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotrialzole, 2-(2'-hydroxy-5'-t-octylphenyl)benzotriazole, 2-(2'-hydroxy-5'-methylphenyl benzotriazole, dibenzalazine, dianisoylmethane, 4-methoxy-4'-t-butyldibenzoylmethane and 5-(3,3-dimethyl-2-norbornylidene)-3-pentane-2-one.

Other chemical components are not particularly limited, and examples thereof may include vitamins such as vitamin A oil, retinol, retinol palmitate, inositol, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), DL-α-tocopherol, DL-α-tocopherol acetate, pantothenic acid, and biotin; hormones such as estradiol and ethynyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor, sulfur, lysozyme chloride, and pyridoxine chloride.

Various kinds of extracts are not particularly limited, and examples thereof may include Houttuynia cordata extract, Phellodendron bark extract, melilot extract, dead nettle extract, licorice extract, peony root extract, soapwort extract, luffa extract, cinchona extract, strawberry geranium extract, sophora root extract, nuphar extract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, hamamelis extract, placenta extract, thymic extract, silk extract, and licorice extract.

Examples of the various kinds of powders may include bright coloring pigments such as red oxide, yellow iron oxide, black iron oxide, mica titanium, iron oxide-coated mica titanium and titanium oxide-coated glass flakes, inorganic powders such as those of mica, talc, kaolin, sericite, titanium dioxide and silica, and organic powders such as polyethylene powder, nylon powder, crosslinked polystyrene, cellulose powder and silicone powder. Preferably, part or all of the powder component is subjected to a hydrophobization treatment with a substance such as a silicone, a fluorine compound, a metallic soap, an oily agent or an acyl glutamic acid salt for improvement of sensory characteristics and improvement of makeup retainability. Other zinc oxide particles that do not fall under the present invention may be mixed and used.

The zinc oxide particles of the present invention can also be used as a heat releasing filler.

Preferably, the zinc oxide particles of the present invention are used in combination with a heat releasing filler having a particle diameter larger than that of the zinc oxide particles of the present invention when used as a heat releasing filler. The filler that can be used in combination is not particularly limited, and examples thereof may include metal oxides such as magnesium oxide, titanium oxide and aluminum oxide, aluminum nitride, boron nitride, silicon carbide, silicon nitride, titanium nitride, metal silicon and diamond. Further, zinc oxide other than the zinc oxide particles described above can be used in combination. The heat releasing filler used in combination may have any shape such as a spherical shape, a needle shape, a rod shape or a plate shape.

When the zinc oxide particles of the present invention are used in combination with other heat releasing fillers, the heat releasing filler that can be used in combination preferably has an average particle diameter of 1 to 100 μm. Combination with such a heat releasing filler having a large particle diameter is preferable because the heat releasing filler of the present invention is filled in gaps, so that the filling rate can be increased.

Preferably, the zinc oxide particles of the present invention are contained in a ratio of 10 to 90% by volume based on the total amount of the heat releasing fillers when the zinc oxide particles of the present invention are used in combination with other heat releasing fillers. By setting the ratio as described above, the filling rate can be increased.

When the zinc oxide particles are used as a heat releasing filler, they can be mixed with a resin and used as a heat releasing resin composition. In this case, the resin to be used may be either a thermoplastic resin or a thermosetting resin, and examples thereof may include resins such as an epoxy resin, a phenol resin, a polyphenylene sulfide (PPS) resin, a polyester-based resin, polyamide, polyimide, polystyrene, polyethylene, polypropylene, polyvinyl chloride, polyvinylidene chloride, a fluororesin, polymethyl methacrylate, an ethylene/ethyl acrylate copolymer (EEA) resin, polycarbonate, polyurethane, polyacetal, polyphenylene ether, polyether imide, an acrylonitrile-butadiene-styrene copolymer (ABS) resin, a liquid crystal resin (LCP), a silicone resin and an acrylic resin.

The heat releasing resin composition of the present invention may be (1) a resin composition for thermoforming, which is obtained by kneading a thermoplastic resin and the zinc oxide particles in a molten state, (2) a resin composition obtained by kneading a thermosetting resin and the zinc oxide particles, followed by heating the mixture to be cured, or (3) a resin composition for coatings, which is obtained by dispersing the zinc oxide particles in a resin solution or dispersion.

When the heat releasing resin composition of the present invention is a resin composition for thermoforming, a resin component can be freely selected according to a use purpose. For example, when the resin composition is bonded and adhered to a heat source and a radiator plate, a resin having high adhesiveness and a low hardness, such as a silicone resin or an acrylic resin, may be selected.

When the heat releasing resin composition of the present invention is a resin composition for coatings, the resin does not necessarily have to have curability. The coating may be a solvent-based coating containing an organic solvent, or a water-based coating with a resin dissolved or dispersed in water.

When the zinc oxide particles are used as a heat releasing filler, they can be mixed with a base oil containing a mineral oil or a synthetic oil, and used as a heat releasing grease. When the zinc oxide particles are used as the heat releasing grease, an α-olefin, a diester, a polyol ester, a trimellitic acid ester, a polyphenyl ether, an alkyl phenyl ether or the like can be used as a synthetic oil. The zinc oxide particles can also be mixed with a silicone oil and used as a heat releasing grease.

When the zinc oxide particles of the present invention are used as a heat releasing filler, other components can also be used in combination. Examples of other components that can be used in combination may include a resin and a surfactant.

The zinc oxide particles of the present invention can be used in the fields of vulcanization accelerators for rubber, pigments for coatings/inks, electronic components such as ferrites and varistors, pharmaceuticals and so on in addition to the cosmetics and heat releasing fillers described above.

EXAMPLES

Hereinafter, the present invention will be explained with reference to examples. However, the present invention is not limited to these examples.

Example 1

Figure 1:
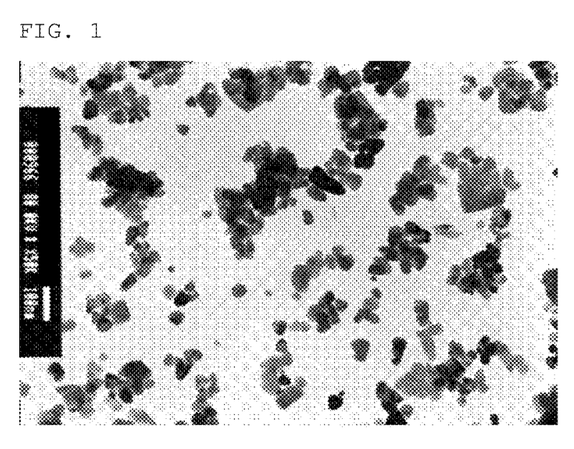
FIG. 1 is a transmission electron microscope photograph of zinc oxide particles of the present invention obtained in Example 1.
Figure 2:
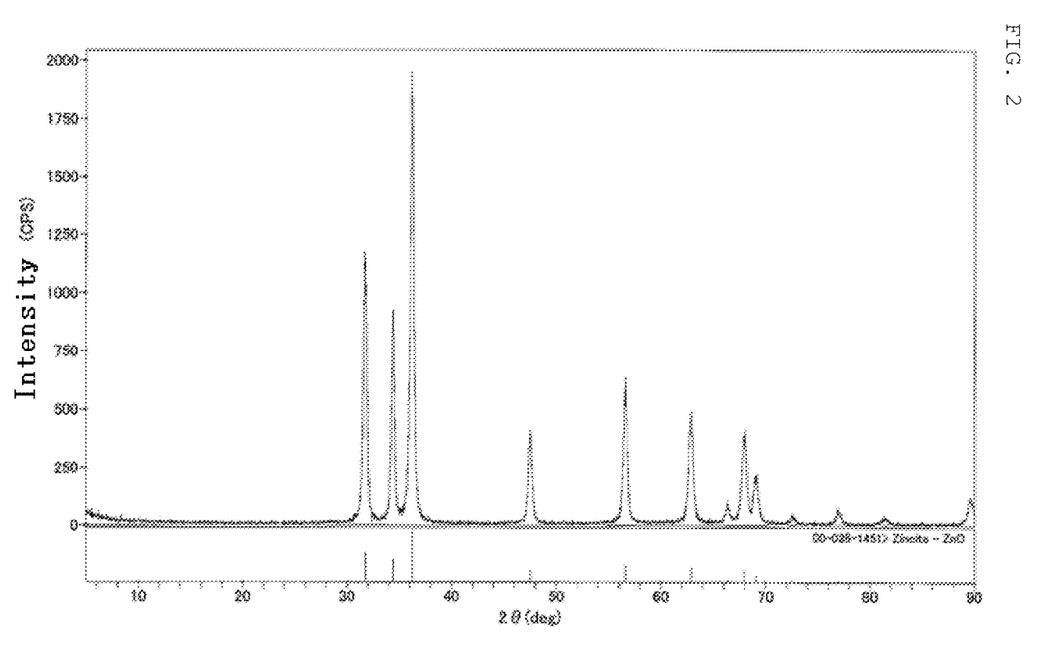
FIG. 2 is an X-ray diffraction spectrum of zinc oxide particles of the present invention obtained in Example 1.

In 1200 ml of an aqueous zinc acetate solution prepared by dissolving 66.51 g of zinc acetate dihydrate (zinc acetate manufactured by Hosoi Chemical Industry Co., Ltd.) in water so as to have a concentration of 0.25 mol/l in terms of zinc acetate dihydrate, 80 g of FINEX-50 (manufactured by Sakai Chemical Industry Co., Ltd., primary particle diameter: 0.020 μm) was repulped, thereby forming a slurry. Subsequently, the slurry was heated to 70° C. over 42 minutes with stirring, and aged at 70° C. for 3 hours with stirring. After aging, the slurry was filtered, and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain zinc oxide particles having a primary particle diameter of 0.046 μm. The size and form of the obtained particles were observed with a transmission electron microscope (TEM, JEM-1200EX II, manufactured by JEOL Ltd.). The obtained electron microscope photograph is shown in FIG. 1. Further, the X-ray diffraction spectrum of the obtained particles is shown in FIG. 2. The results of evaluating the physical properties of the obtained particles and the physical properties of the coating film are shown in Table 1.

Example 2

Figure 3:
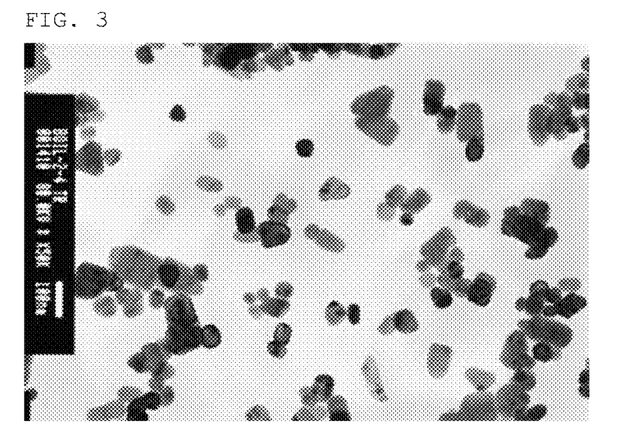
FIG. 3 is a transmission electron microscope photograph of zinc oxide particles of the present invention obtained in Example 2.

In 1200 ml of an aqueous zinc acetate solution prepared by dissolving 93.12 g of zinc acetate dihydrate (zinc acetate manufactured by Hosoi Chemical Industry Co., Ltd.) in water so as to have a concentration of 0.35 mol/l in terms of zinc acetate dihydrate, 80 g of FINEX-50 (manufactured by Sakai Chemical Industry Co., Ltd., primary particle diameter: 0.020 μm) was repulped, thereby forming a slurry. Subsequently, the slurry was heated to 90° C. over 54 minutes with stirring, and aged at 90° C. for 3 hours with stirring. After aging, the slurry was filtered, and washed with water. Subsequently, the obtained solid was repulped in 3 liters of water to form a slurry, and the slurry was heated to 90° C. over 54 minutes with stirring, and heated and washed at 90° C. for 30 minutes with stirring. After heating and washing, the slurry was filtered, washed with water, and dried at 110° C. for 12 hours to obtain zinc oxide particles having a primary particle diameter of 0.074 μm. The size and form of the obtained particles were observed with a transmission electron microscope (TEM, JEM-1200EX II, manufactured by JEOL Ltd.). The obtained electron microscope photograph is shown in FIG. 3. The results of evaluating the physical properties of the obtained particles and the physical properties of the coating film are shown in Table 1.

Example 3

Figure 4:
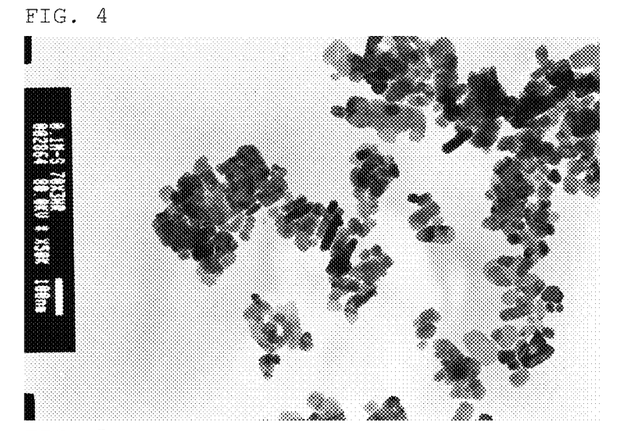
FIG. 4 is a transmission electron microscope photograph of zinc oxide particles of the present invention obtained in Example 3.

In 1200 ml of an aqueous zinc acetate solution prepared by dissolving 26.61 g of zinc acetate dihydrate (zinc acetate manufactured by Hosoi Chemical Industry Co., Ltd.) in water so as to have a concentration of 0.10 mol/l in terms of zinc acetate dihydrate, 80 g of FINEX-50 (manufactured by Sakai Chemical Industry Co., Ltd., primary particle diameter: 0.020 μm) was repulped, thereby forming a slurry. Subsequently, the slurry was heated to 70° C. over 84 minutes with stirring, and aged at 70° C. for 3 hours with stirring. After aging, the slurry was filtered, and washed with water. Subsequently, the obtained solid was repulped in 3 liters of water to form a slurry, and the slurry was heated to 70° C. over 84 minutes with stirring, and heated and washed at 70° C. for 30 minutes with stirring. After heating and washing, the slurry was filtered, washed with water, and dried at 110° C. for 12 hours to obtain zinc oxide particles having a primary particle diameter of 0.045 μm. The size and form of the obtained particles were observed with a transmission electron microscope (TEM, JEM-1200EX II, manufactured by JEOL Ltd.). The obtained electron microscope photograph is shown in FIG. 4. The results of evaluating the physical properties of the obtained particles and the physical properties of the coating film are shown in Table 1.

Comparative Example 1

Figure 5:
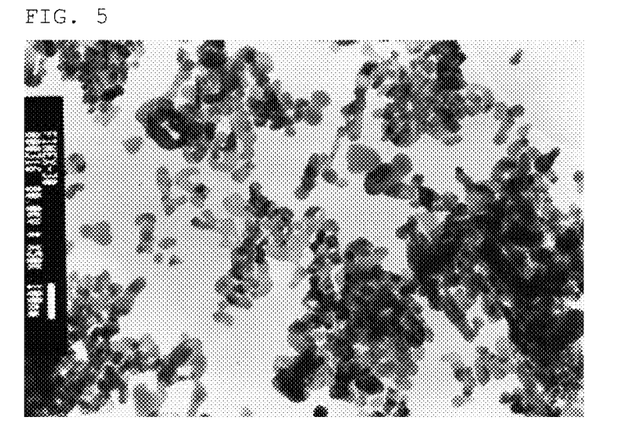
FIG. 5 is a transmission electron microscope photograph of zinc oxide particles (FINEX-30 manufactured by Sakai Chemical Industry Co., Ltd.) used in Comparative Example 1.

FINEX-30 (manufactured by Sakai Chemical Industry Co., Ltd., primary particle diameter: 0.044 μm) was evaluated in the same manner as in the examples. The electron microscope photograph is shown in FIG. 5. The results of evaluating the physical properties of the obtained particles and the physical properties of the coating film are shown in Table 1.

Comparative Example 2

Figure 6:
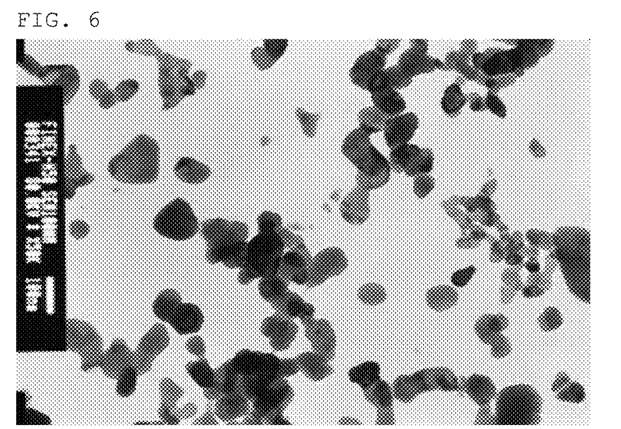
FIG. 6 is a transmission electron microscope photograph of zinc oxide particles obtained in Comparative Example 2.

In an alumina crucible (length/width/height=100 mm/100 mm/35 mm) was put 10 g of FINEX-50 (manufactured by Sakai Chemical Industry Co., Ltd., particle diameter: 0.020 μm), and left standing and calcinated at 500° C. for 2 hours in an electric muffle furnace (manufactured by TOYO ENGINEERING WORKS, LTD.) to obtain zinc oxide particles having a primary particle diameter of 0.083 μm. The size and form of the obtained particles were observed with a transmission electron microscope (TEM, JEM-1200EX II, manufactured by JEOL Ltd.). The obtained electron microscope photograph is shown in FIG. 6. The results of evaluating the physical properties of the obtained particles and the physical properties of the coating film are shown in Table 1.

Comparative Example 3

Figure 7:
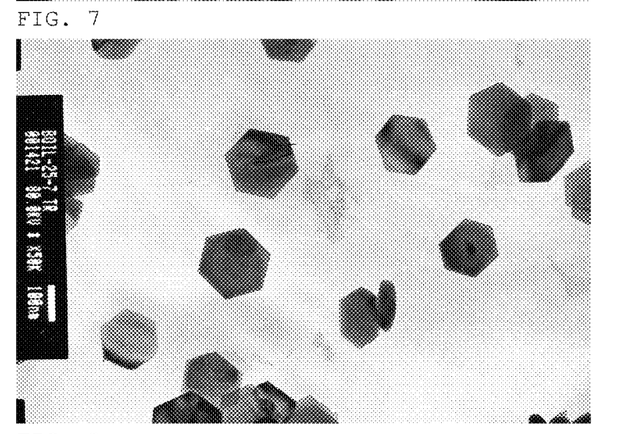
FIG. 7 is a transmission electron microscope photograph of hexagonal plate-shaped zinc oxide particles obtained in Comparative Example 3.

In 1200 ml of an aqueous zinc acetate solution prepared by dissolving 133.02 g of zinc acetate dihydrate (zinc acetate manufactured by Hosoi Chemical Industry Co., Ltd.) in water so as to have a concentration of 0.5 mol/l in terms of zinc acetate dihydrate, 80 g of FINEX-50 (manufactured by Sakai Chemical Industry Co., Ltd., particle diameter: 0.020 μm) was repulped, thereby forming a slurry. Subsequently, the slurry was heated to 70° C. over 42 minutes with stirring, and aged at 70° C. for 3 hours with stirring. After aging, the slurry was quenched immediately, then filtered and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain hexagonal plate-shaped zinc oxide particles having a primary particle diameter of 0.112 μm. The size and form of the obtained particles were observed with a transmission electron microscope (TEM, JEM-1200EX II, manufactured by JEOL Ltd.). The obtained electron microscope photograph is shown in FIG. 7. The results of evaluating the physical properties of the obtained particles and the physical properties of the coating film are shown in Table 1.

Comparative Example 4

Figure 8:
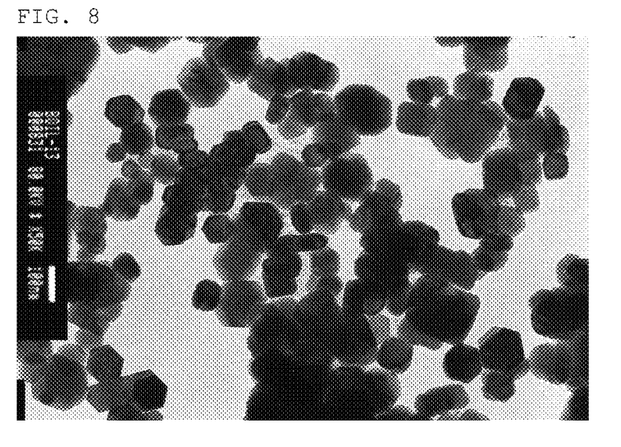
FIG. 8 is a transmission electron microscope photograph of hexagonal prism-shaped zinc oxide particles obtained in Comparative Example 4.

In 1200 ml of an aqueous zinc acetate solution prepared by dissolving 106.42 g of zinc acetate dihydrate (zinc acetate manufactured by Hosoi Chemical Industry Co., Ltd.) in water so as to have a concentration of 0.4 mol/l in terms of zinc acetate dihydrate, 80 g of SF-15 (zinc oxide fine particles manufactured by Sakai Chemical Industry Co., Ltd., particle diameter: 0.075 μm) was repulped, thereby forming a slurry. Subsequently, the slurry was heated to 70° C. over 42 minutes with stirring, and aged at 70° C. for 5 hours with stirring. After aging, the slurry was filtered, and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain hexagonal prism-shaped zinc oxide particles having a primary particle diameter of 0.131 μm. The size and form of the obtained particles were observed with a transmission electron microscope (TEM, JEM-1200EX II, manufactured by JEOL Ltd.). The obtained electron microscope photograph is shown in FIG. 8. The results of evaluating the physical properties of the obtained particles and the physical properties of the coating film are shown in Table 1.

(X-Ray Diffraction Spectrum and Composition of Obtained Particles)

The X-ray diffraction spectrum shown in FIG. 2 and the compositions of the obtained particles in Table 1 show results of performing analysis using an X-ray diffractometer UltimaIII (manufactured by Rigaku Corporation) having an X-ray tube with copper.

(Crystallite Diameter)

For the crystallite diameter (μm) herein, results of performing analysis using an X-ray diffractometer UltimaIII (manufactured by Rigaku Corporation) having an X-ray tube with copper are shown. The crystallite usually means a small single crystal in a microscopic level, which forms a crystalline substance. Herein, the crystallite diameter (μm) is a value determined from a half width of a diffraction peak of the (101) plane of zinc oxide in the X-ray diffraction pattern of a hexagonal wurtzite-type zinc oxide particle.

(Primary Particle Diameter)

The primary particle diameter corresponds to a diameter of a sphere having the same surface area as a specific surface area determined by a BET method. That is, the primary particle diameter is a value determined according to the relational expression:

$$\text{primary particle diameter (μm)} = [6/(Sg \times \rho)]$$

($Sg$ (m$^2$/g): specific surface area, $\rho$ (g/cm$^3$): true specific gravity of particle.

The specific surface area: $Sg$ by the BET method was measured using a fully automatic BET specific surface area measuring device Macsorb (manufactured by Mountech Co., Ltd.), and the measurement value was used for the calculation described above. As the true specific gravity of particle: $\rho$, a value of the true specific gravity of zinc oxide, i.e. 5.6, was used for the above calculation.

(Crystallite Diameter/Primary Particle Diameter)

A value shown as crystallite diameter/primary particle diameter herein is a value as an indicator of a level of independency of primary particles that form a powder. The primary particle diameter is a geometric particle diameter corresponding to a diameter of a sphere having the same surface area as a specific surface area determined by a BET method as described previously. On the other hand, the crystallite diameter is a value determined from a half width of a diffraction peak of the (101) plane of zinc oxide in the X-ray diffraction pattern as described previously. Therefore, as the value of crystallite diameter/primary particle diameter becomes closer to 1, a difference between the geometric particle diameter and the single crystal size decreases, which means that primary particles are not aggregated particles, but exist independently as single crystal particles.

(Aspect Ratio)

A ratio between a major axis and a minor axis passing through the center of major axis: major axis/minor axis was measured for 250 primary particles of zinc oxide particles in a visual field of 20000 to 50000 magnification in a transmission electron microscope (TEM, JEM-1200EX II, manufactured by JEOL Ltd.) photograph, and an average value of a cumulative distribution thereof was defined as an aspect ratio.

(Oil Absorption)

The oil absorption was measured by the method described in Pigment Test Method-Oil Absorption in JIS K 5101-13-2. As an oil, isopropyl myristate (EXCEPARL IPM manufactured by Kao Corporation) was used in place of boiled linseed oil.

(BET Specific Surface Area)

The BET specific surface area ($m^2/g$) is a value measured using a fully automatic BET specific area measuring device Macsorb (manufactured by Mountech Co., Ltd.), and corresponds to a specific surface area: Sg used for calculation of the primary particle diameter.

(Oil Absorption/BET Specific Surface Area)

The oil absorption/BET specific surface area (ml/100 $m^2$) is a value obtained by dividing the value of the oil absorption (ml/100 g) by the value of the BET specific surface area ($m^2/g$), and as this value becomes smaller, the oil absorption per unit area of the particle surface is low, leading to reduced aggregation of particles and enhanced dispersibility of particles.

(Apparent Density)

The apparent density is a value measured by the method described in Pigment Test Method-Apparent Density or Apparent Specific Volume (Standing Method) in JIS K 5101-12-1. The volume of the powder decreases as the apparent density increases.

(Preparation of Coating Film)

In a mayonnaise bottle having a volume of 75 ml, 2 g of zinc oxide particles in each of examples and comparative examples described above, 10 g of varnish (ACRYDIC A-801-P manufactured by DIC Corporation), 5 g of butyl acetate (special grade reagent, manufactured by Wako Pure Chemical Industries, Ltd.), 5 g of xylene (genuine special grade, manufactured by JUNSEI CHEMICAL CO., LTD.) and 38 g of glass beads (1.5 mm, manufactured by Potters-Ballotini Co., Ltd.) were put and sufficiently mixed, then fixed in a paint conditioner Model 5410 (manufactured by RED DEVIL, Inc.), and subjected to a dispersion treatment by giving vibrations for 90 minutes, thereby preparing a coating. Next, a small amount of the prepared coating was added dropwise onto a slide glass (length/width/thickness=76 mm/26 mm/0.8 to 1.0 mm, manufactured by Matsunami Glass Ind., Ltd.), and a coating film was prepared using a bar coater (No. 579 ROD No. 6, manufactured by YASUDA SEIKI SEISAKUSHO, LTD.). The prepared coating film was dried at 20° C. for 12 hours, and then used for measurement of total light transmittance 1, total light transmittance 2, parallel light transmittance 1, parallel light transmittance 2 and sharpened gloss (20° gloss).

(Total Light Transmittance 1, Total Light Transmittance 2, Parallel Light Transmittance 1 and Parallel Light Transmittance 2)

Herein, total light transmittance 1(%), total light transmittance 2(%), parallel light transmittance 1(%) and parallel light transmittance 2(%) are values obtained by measuring the prepared coating film using a spectrophotometer V-570 (manufactured by JASCO Corporation). The value of total light transmittance 1(%) is a value of total light transmittance at a wavelength of 310 nm, the value of total light transmittance 2(%) is a value of total light transmittance at a wavelength of 350 nm, the value of parallel light transmittance 1(%) is a value of parallel light transmittance at a wavelength of 500 nm, and the value of parallel light transmittance 2(%) is a value of parallel light transmittance at a wavelength of 700 nm. An ultraviolet blocking effect to ultraviolet rays having a wavelength of UVB is enhanced as the value of total light transmittance 1(%) becomes smaller, and an ultraviolet blocking effect to ultraviolet rays having a wavelength of UVA is enhanced as the value of total light transmittance 2(%) becomes smaller. Visible light transparency is enhanced as the values of parallel light transmittance 1(%) and parallel light transmittance 2(%) become larger.

(Sharpened gloss (20° Gloss))

Herein, the sharpened gloss (20° gloss) of the coating film is a value obtained by measuring the coating film using GLOSS METER GM-26D (manufactured by MURAKAMI COLOR RESEARCH LABORATORY CO., Ltd.), and is a value of glossiness at an incidence angle of 20°. A larger value of sharpened gloss (20° gloss) corresponds to reduced aggregation and enhanced dispersibility of zinc oxide particles in the prepared coating film.

TABLE 1

| | | Example 1 | Example 2 | Example 3 | Comparative Example 1 | Comparative Example 2 | Comparative Example 3 | Comparative Example 4 |
|---|---|---|---|---|---|---|---|---|
| Preparation conditions | Zinc oxide fine particles as raw material | FINEX-50 | FINEX-50 | FINEX-50 | FINEX-30 | FINEX-50 | FINEX-50 | SF-15 |
| | Particle diameter of raw material (μm) | 0.020 | 0.020 | 0.020 | 0.044 | 0.020 | 0.020 | 0.075 |
| | Amount of raw material used in preparation (g) | 80 | 80 | 80 | | | 80 | 80 |
| | Zinc salt used in preparation | Zinc acetate dihydrate | Zinc acetate dihydrate | Zinc acetate dihydrate | | | Zinc acetate dihydrate | Zinc acetate dihydrate |
| | Amount of zinc salt (g) | 66.51 | 93.12 | 26.61 | | | 133.02 | 106.42 |
| | Solvent used in preparation | Water | Water | Water | | | Water | Water |
| | Amount of zinc salt solution (ml) | 1200 | 1200 | 1200 | | | 1200 | 1200 |
| | Concentration of zinc salt solution (mol/l) | 0.25 | 0.35 | 0.10 | | | 0.50 | 0.40 |
| | Aging temperature (° C.) | 70 | 90 | 70 | | | 70 | 70 |
| | Aging time (Hr) | 3 | 3 | 3 | | | 3 | 5 |
| | Calcinating temperature/ calcinating time | | | | | 500° C./2 Hr | | |

TABLE 1-continued

|  |  | Example 1 | Example 2 | Example 3 | Comparative Example 1 | Comparative Example 2 | Comparative Example 3 | Comparative Example 4 |
|---|---|---|---|---|---|---|---|---|
| Physical properties of particles | Composition of obtained particles | Zinc oxide | Zinc oxide | Zinc oxide | Zinc oxide | Zinc oxide | Zinc oxide | Zinc oxide |
|  | Primary particle diameter ($\mu$m) | 0.046 | 0.074 | 0.045 | 0.044 | 0.083 | 0.112 | 0.131 |
|  | Crystallite diameter ($\mu$m) | 0.036 | 0.057 | 0.032 | 0.031 | 0.054 |  |  |
|  | Crystallite diameter/primary particle diameter | 0.78 | 0.77 | 0.71 | 0.70 | 0.65 |  |  |
|  | Aspect ratio | 1.3 | 1.4 | 1.4 | 2.0 | 1.8 | 3.5 | 1.2 |
|  | BET specific surface area (m$^2$/g) | 23.1 | 14.5 | 23.6 | 24.3 | 12.9 | 9.6 | 8.2 |
|  | Oil absorption (ml/100 g) | 26 | 18 | 27 | 43 | 34 | 26 | 23 |
|  | Oil absorption/BET specific surface area (ml/100 m$^2$) | 1.13 | 1.24 | 1.14 | 1.77 | 2.63 | 2.72 | 2.81 |
|  | Apparent density (g/ml) | 0.53 | 0.66 | 0.49 | 0.13 | 0.16 | 0.75 | 0.59 |
| Physical properties of coating film | Total light transmittance 1 (%) | 14 | 16 | 10 | 13 | 16 | 13 | 12 |
|  | Total light transmittance 2 (%) | 13 | 15 | 11 | 13 | 15 | 10 | 10 |
|  | Parallel light transmittance 1 (%) | 84 | 78 | 89 | 78 | 76 | 55 | 56 |
|  | Parallel light transmittance 2 (%) | 93 | 92 | 97 | 90 | 87 | 83 | 81 |
|  | Sharpened gloss (20° gloss) | 148 | 143 | 151 | 109 | 99 |  | 125 |

Table 1 shows that the zinc oxide particles of the present invention have a very low oil absorption as compared to conventional zinc oxide particles shown in Comparative Examples 1 and 2, and is excellent in dispersibility and transparency. It is also evident that the zinc oxide particles of the present invention have a high apparent density as compared to conventional zinc oxide particles shown in Comparative Examples 1 and 2, and is thus a small volume as a powder. When a reaction was carried out under the conditions of Comparative Example 3, hexagonal plate-shaped zinc oxide particles were formed, and the zinc oxide particles of the present invention could not be obtained. When a reaction was carried out under the conditions of Comparative Example 4, hexagonal prism-shaped zinc oxide particles were formed, and the zinc oxide particles of the present invention could not be obtained.

INDUSTRIAL APPLICABILITY

The zinc oxide particles of the present invention can be used as a component of a cosmetic, a heat releasing filler, a heat releasing resin composition, a heat releasing grease and a heat releasing coating composition.

The invention claimed is:

1. Zinc oxide particles having a primary particle diameter of less than 0.1 $\mu$m, an aspect ratio of less than 2.5 and an oil absorption/BET specific surface area of 1.5 ml/100 m$^2$ or less, and having a sharpened gloss (20° gloss) of 110 or more as a coating film.

2. The zinc oxide particles according to claim 1, which are obtained by aging zinc oxide fine particles in water in which a zinc salt is dissolved.

3. The zinc oxide particles according to claim 2, which have a total light transmittance of 20% or less at a wavelength of 310 nm, a total light transmittance of 20% or less at a wavelength of 350 nm, a parallel light transmittance of 70% or more at a wavelength of 500 nm and a parallel light transmittance of 70% or more at a wavelength of 700 nm.

4. A method for production of the zinc oxide particles according to claim 3, comprising a step of aging zinc oxide fine particles having a particle diameter of 0.005 $\mu$m or more and 0.05 $\mu$m or less in water at 45 to 110° C. in which a zinc salt is dissolved in an amount of 0.005 mol/l or more and less than 0.30 mol/l.

5. The zinc oxide particles according to claim 2, which have an apparent density of 0.26 g/ml or more.

6. A method for production of the zinc oxide particles according to claim 5, comprising a step of aging zinc oxide fine particles having a particle diameter of 0.005 $\mu$m or more and 0.05 $\mu$m or less in water at 45 to 110° C. in which a zinc salt is dissolved in an amount of 0.005 mol/l or more and less than 0.30 mol/l.

7. A method for production of the zinc oxide particles according to claim 2, comprising a step of aging zinc oxide fine particles having a particle diameter of 0.005 $\mu$m or more and 0.05 $\mu$m or less in water at 45 to 110° C. in which a zinc salt is dissolved in an amount of 0.005 mol/l or more and less than 0.30 mol/l.

8. The zinc oxide particles according to claim 1, which have a total light transmittance of 20% or less at a wavelength of 310 nm, a total light transmittance of 20% or less at a wavelength of 350 nm, a parallel light transmittance of 70% or more at a wavelength of 500 nm and a parallel light transmittance of 70% or more at a wavelength of 700 nm.

9. The zinc oxide particles according to claim 8, which have an apparent density of 0.26 g/ml or more.

10. A method for production of the zinc oxide particles according to claim 9, comprising a step of aging zinc oxide fine particles having a particle diameter of 0.005 $\mu$m or more and 0.05 $\mu$m or less in water at 45 to 110° C. in which a zinc salt is dissolved in an amount of 0.005 mol/l or more and less than 0.30 mol/l.

11. A method for production of the zinc oxide particles according to claim 8, comprising a step of aging zinc oxide fine particles having a particle diameter of 0.005 $\mu$m or more and 0.05 $\mu$m or less in water at 45 to 110° C. in which a zinc salt is dissolved in an amount of 0.005 mol/l or more and less than 0.30 mol/l.

12. The zinc oxide particles according to claim 1, which have an apparent density of 0.26 g/ml or more.

13. A method for production of the zinc oxide particles according to claim 12, comprising a step of aging zinc oxide fine particles having a particle diameter of 0.005 μm or more and 0.05 μm or less in water at 45 to 110° C. in which a zinc salt is dissolved in an amount of 0.005 mol/l or more and less than 0.30 mol/l.

14. A method for production of the zinc oxide particles according to claim 1, comprising a step of aging zinc oxide fine particles having a particle diameter of 0.005 μm or more and 0.05 μm or less in water at 45 to 110° C. in which a zinc salt is dissolved in 0.005 mol/l or more and less than 0.30 mol/l.

15. A cosmetic comprising the zinc oxide particles according to claim 1.

16. A heat releasing filler comprising the zinc oxide particles according to claim 1.

17. A heat releasing resin composition comprising the zinc oxide particles according to claim 1.

18. A heat releasing grease comprising the zinc oxide particles according to claim 1.

19. A heat releasing coating composition comprising the zinc oxide particles according to claim.

* * * * *